United States Patent [19]
DeVries et al.

[11] Patent Number: 6,152,135
[45] Date of Patent: Nov. 28, 2000

[54] VENTILATOR SYSTEM

[75] Inventors: Douglas F. DeVries, Redlands; Michael B. Holmes, Riverside, both of Calif.

[73] Assignee: Pulmonetic Systems, Inc., Colton, Calif.

[21] Appl. No.: 09/178,466

[22] Filed: Oct. 23, 1998

[51] Int. Cl.[7] ........................................ A62B 9/02
[52] U.S. Cl. ........................ 128/205.24; 128/204.18
[58] Field of Search ................... 251/12, 14, 66, 251/129.01, 129.08, 142, 205, 206, 289, 336, 356; 128/204.18, 204.21, 205.24, 207.12, 206.15

[56] References Cited

U.S. PATENT DOCUMENTS

| | | | |
|---|---|---|---|
| 4,524,947 | 6/1985 | Barnes et al. | 251/129 |
| 4,957,107 | 9/1990 | Sipin | 128/204.21 |
| 4,967,781 | 11/1990 | Baron | 137/82 |
| 5,020,771 | 6/1991 | Nakatsukasa et al. | 251/129.08 |
| 5,237,987 | 8/1993 | Anderson et al. | 128/204.18 |
| 5,241,955 | 9/1993 | Dearman et al. | 128/204.18 |
| 5,271,389 | 12/1993 | Isaza et al. | 128/204.21 |
| 5,316,261 | 5/1994 | Stoner | 251/205 |
| 5,881,722 | 3/1999 | DeVries et al. | 128/204.21 |
| 5,931,159 | 8/1999 | Suzuki et al. | 128/204.18 |

*Primary Examiner*—Glenn K. Dawson
*Attorney, Agent, or Firm*—Klein & Szekeres, LLP

[57] ABSTRACT

A portable mechanical ventilator uses a constant-speed compressor compressor and a recirculating bypass circuit. Bypass flow is governed by a spring-biased bypass valve so connected to both the inlet and the outlet of the main flow control valve as to maintain a differential pressure across the flow valve sufficient to operate the ventilator with minimal energy consumption. The flow valve is operated by a microprocessor in accordance with empirically derived lookup tables to both produce the desired air flow and provide a measure of that air flow.

16 Claims, 4 Drawing Sheets

VENTILATOR SYSTEM

FIELD OF THE INVENTION

This invention relates to ventilators for patients requiring breathing assistance, and more particularly to a ventilator system which uses a continuously running compressor with a recirculating bypass valve and a computerized main valve control that maintains a constant pressure differential across the main valve.

BACKGROUND OF THE INVENTION

Low pressure rotary compressor type ventilators, for patients who cannot breathe on their own or need assistance in breathing conventionally use either a variable-speed compressor or a constant speed compressor. The former type is exemplified by U.S. Pat. No. 5,694,926 to DeVries et al. and operates by rapidly accelerating from essentially a standstill to produce an inhalation, and then stopping or decelerating to a basal flow level to allow the patient to exhale. The rapid acceleration and braking requires expensive low inertia compressor mechanisms and requires the compressor's drive circuitry to handle very high currents. This in turn requires bulky and expensive power systems and considerable standby battery power when the ventilator is not connected to the commercial power line.

A constant speed compressor such as that shown in U.S. Pat. No. 4,957,107 to Sipin solves this problem but creates another because of the fact that it dumps substantial quantities of air during the exhalation period. This not only causes the compressor to do unnecessary work, but if the inhalation air is oxygenated, it wastes a great deal of oxygen unless the oxygen supply is sealed off during exhalation. Also, such a system as exemplified by U.S. Pat. No. 4,957,107 is inflexible in that air delivery is either on or off, and cannot be varied during a breath to produce complex inspiration pressure and flow curves.

In general, prior art ventilators tend to be relatively large and heavy and allow the patient little mobility; or, if small and light, they tend to be limited in their ventilation capabilities. It is therefore desirable to provide a relatively small and light ventilator system that can be conveniently carried on the back of a wheelchair or even on a person, and that is versatile yet economical in terms of power consumption. Such a device is not currently available.

SUMMARY OF THE INVENTION

The present invention fills the need described above by providing a ventilator with a continuously running compressor whose output is recirculated during exhalation through a bypass valve. Inspirational flow is controlled by a flow valve operated by a digital step motor operated by a microprocessor. A bypass valve maintains a relatively constant pressure differential across the flow valve while returning the excess compressor flow to the intake side, thus insuring a minimum expenditure of energy. The microprocessor controls the flow valve in accordance with empirically generated lookup tables by continuously iteratively computing the valve position needed to produce a desired flow, taking into account changes in the pressure differential across the flow valve. The flow valve thus functions as both the flow control and the flow feedback, with a high degree of accuracy. The inventive arrangement avoids loss of oxygen, yet allows the use of a constant speed compressor so as to produce a versatile ventilator with small, readily portable components. A novel advantage of the ventilator of this invention is that it is capable of operating in both volume and pressure control modes with a single constant-speed compressor.

DESCRIPTION OF THE PREFERRED EMBODIMENT

Figure 1:
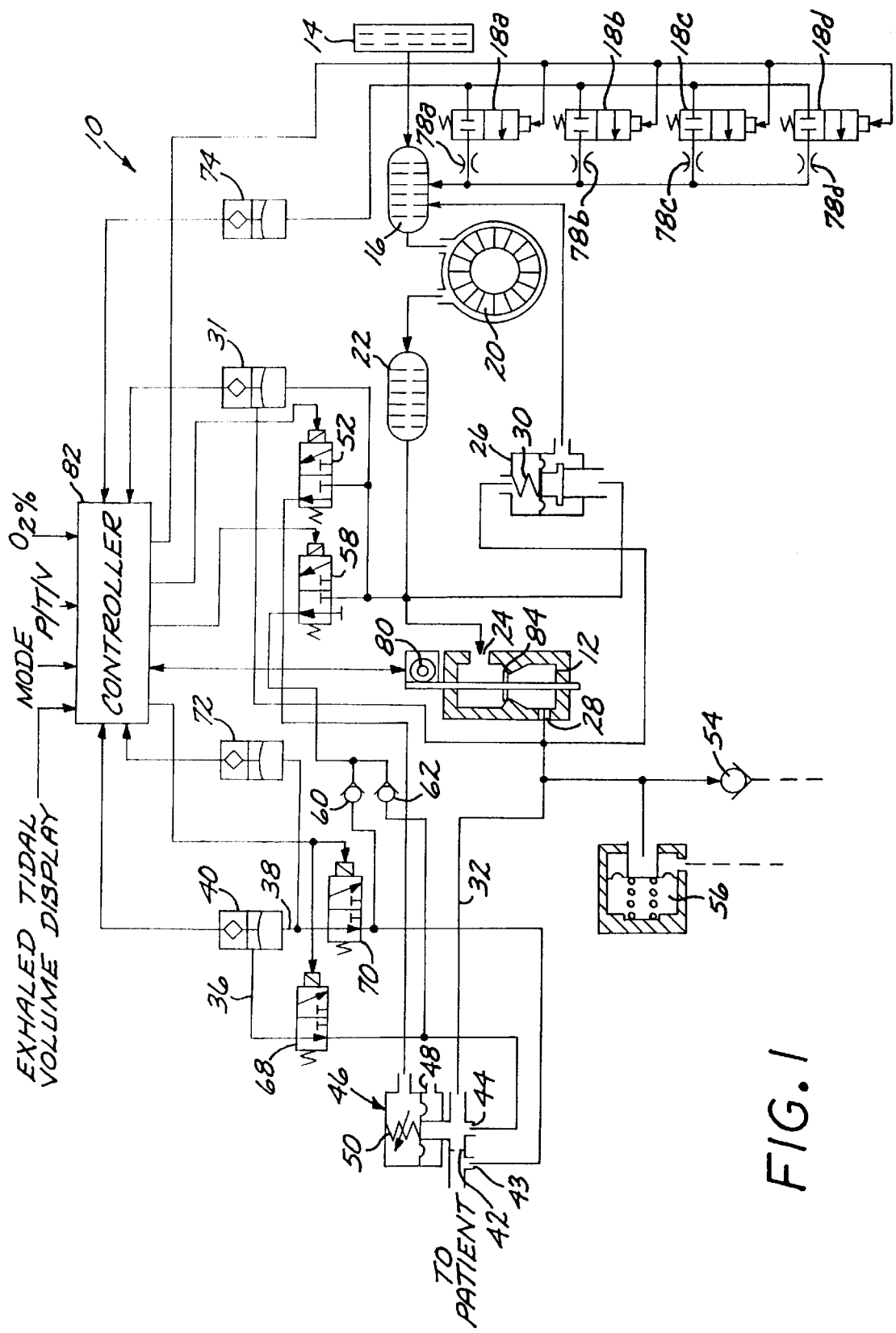
FIG. 1 is a schematic diagram of the ventilator of this invention.
Figure 2:
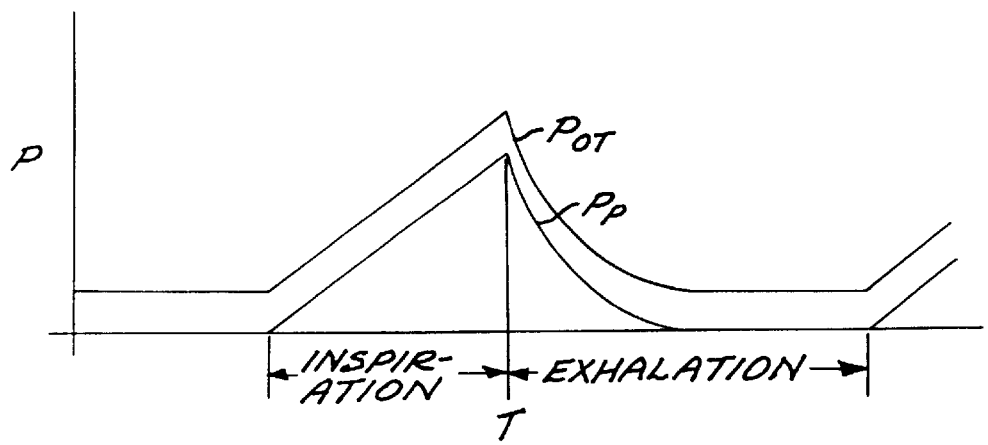
FIG. 2 is a time-pressure diagram illustrating the constance of the pressure differential across the flow valve throughout a breathing cycle.

FIG. 1 schematically shows the mechanical portion of the inventive ventilator 10. The ventilator 10 is an electromechanical ventilator capable of providing positive pressure ventilatory support to patients in a variety of modes.

Specifically, the following breath types are supported:
a) Volume-controlled breaths, in which a pre-set tidal volume of air is delivered in a pre-set inspiratory time during each breath, and a breath is initiated either by the patient or by a timing circuit;
b) Pressure breaths, in which a sufficient flow is maintained to produce a pre-set inspiration pressure of up to 99 cm $H_2O$ during inspiration; a breath is initiated by the patient or ventilator; and the inspiration is terminated when the flow drops to a predetermined level, or when a timing algorithm times out;
c) Spontaneous breaths, in which the inspiratory flow is varied as required to meet patient demand and maintain a constant baseline pressure; a breath is initiated by the patient; and the inspiration is terminated when flow drops to a predetermined level, or the set backup time expires, whichever occurs first.

It is one of the features of the invention that the ventilator 10 can operate in conventional flow-terminated or time-terminated pressure or spontaneous breath modes, or in a conventional tidal volume mode, without any change in the compressor action or speed (during a breath), merely by appropriately activating the flow valve 12.

Ambient air enters the ventilator 10 through an inlet filter 14 and proceeds to an accumulator/silencer 16 where it is optionally mixed with oxygen at a rate set by solenoid valves 18a–d. The accumulator/silencer 16 also conventionally reduces the compressor noise during operation. Oxygenated air is drawn from accumulator/silencer 16 by a constant-speed compressor 20 which is preferably a drag compressor adjusted to run at a speed sufficient to satisfy the maximum demand of the ventilator 10. The output flow and pressure $P_{OT}$ of the compressor 20 is conveyed to the silencer 22 whose output is in turn applied to the input 24 of the flow valve 12.

Except at maximum demand, there will always be at least some surplus oxygenated air that is not needed to supply the flow valve 12. This surplus air is recirculated through bypass valve 26 back into the accumulator/silencer 16, thereby reducing the need for fresh oxygen.

The bypass valve 26 is biased toward the closed position by the combination of the patient air pressure $P_P$ at the output side 28 of flow valve 12 and the pressure of a spring 30 which preferably provides a fixed closing bias of about 10–15 cm $H_2O$. Because the bypass valve 26 thus does not open until $P_{OT}$ overcomes the sum of $P_P$ and the spring bias, the bypass valve 26 tries to maintain a constant pressure differential of about 10–15 cm $H_2O$ between the inlet 24 and outlet 28 of the flow valve 12. This differential is monitored by the transducer 31.

The outlet side 28 of the flow valve 12 is directly connected to the patient through a conduit 32 in which a fixed orifice 42 is interposed. By connecting the inputs 36 and 38 of a differential transducer 40 to a point 43 and a point 44 on opposite sides of the orifice 42, the air flow rate to and from the patient can be measured.

An exhalation valve 46 provides an open path to atmosphere at 48 when, during exhalation, the exhalation pressure exerted by the patient exceeds the bias of adjustable spring 50, and the exhalation drive solenoid valve 52 is in the position shown in FIG. 1. During inspiration, the exhalation valve 46 is locked closed by the solenoid valve 52 which, when energized, applies the flow valve input pressure $P_{OT}$ to the spring chamber of exhalation valve 46. Inasmuch as $P_{OT}$, for reasons discussed above, is always higher than the pressure $P_P$ in conduit 32, no air can escape through outlet 48 during inspiration.

A sub-ambient relief valve 54 is provided in ventilator 10 to allow the patient to inhale in case of a compressor failure. Also, a spring-biased overpressure relief valve 56 limits the pressure $P_P$ to a safe value in case the ventilator flow delivery system fails.

Inasmuch as the intakes 42, 44 of the flow-measuring transducer 40 are prone to clogging due to moisture in the patient's breath, a purge solenoid 58 is periodically momentarily activated to inject air at the pressure $P_{OT}$ into the conduit 32 through apertures 42, 44 and so to keep them clear. Check valves 60, 62 separate the two inputs of transducer 40 in the absence of a purge flow.

For calibration purposes, the auto-zeroing solenoid valves 68, 70 are periodically activated to disconnect the transducer 40 from its inputs 42, 44. Under those conditions, the reading of transducer 40 should be zero. If it is not, the offset signal level of transducer 40 is appropriately compensated for by the controller 82. An airway pressure transducer 72 is connected to the inlet 38 to measure the actual pressure in the patient's airway on the patient side of orifice 42. Also, an oxygen pressure transducer 74 may be provided to measure the oxygen pressure at the supply port 76 and thereby provide data for the automatic adjustment of the oxygen volume fed into the accumulator/silencer 16 through the fixed orifices 78a–d.

The flow valve 12 is digitally operated by a step motor 80. The step motor 80 is driven by a controller microprocessor 82. The inputs to microprocessor 82 are the outputs of transducers 31 (flow valve differential), 40 (airway flow), 72 (airway pressure) and 74 (oxygen pressure), as well as the desired settings of operational mode; breath rate, time, pressure and/or volume parameters; and oxygen concentration. The outputs of the controller 82 are the actuation signals for the solenoids 18a–d (oxygen flow), 52 (exhalation control), 58 (flow sensor purge) and 68, 70 (auto-zero), as well as the digital control signal to the step motor 80 which drives the flow valve 12.

The control of the step motor 80, and thereby of valve 12, is the most critical and most complex operation the controller 82 has to perform. The controller 82 operates the valve positioning motor 80 in accordance with a pair of look-up tables which are empirically generated as follows:

The airway flow f is determined by the differential pressure dp across the flow valve 12 and the area a of the valve orifice 84:

$$f \, \alpha^{\sqrt{}} \, \overline{dp} \tag{1}$$

Since the valve orifice area a is determined by the step motor position, the flow f can be expressed as a function of the differential pressure dp and the step motor position x.

$$f \, x^{\sqrt{}} \, \overline{dp} \tag{2}$$

To improve the accuracy, the actual flow is measured for various combinations of position and differential pressure. This results in a characterization or lookup table (FIG. 4) that gives flow as a function of the output of transducer 31 and the commanded position x of the step motor 80.

The measured characterization table is coarser than what is needed in actual operation, but intermediate values can readily be ascertained by interpolation.

Figure 4:
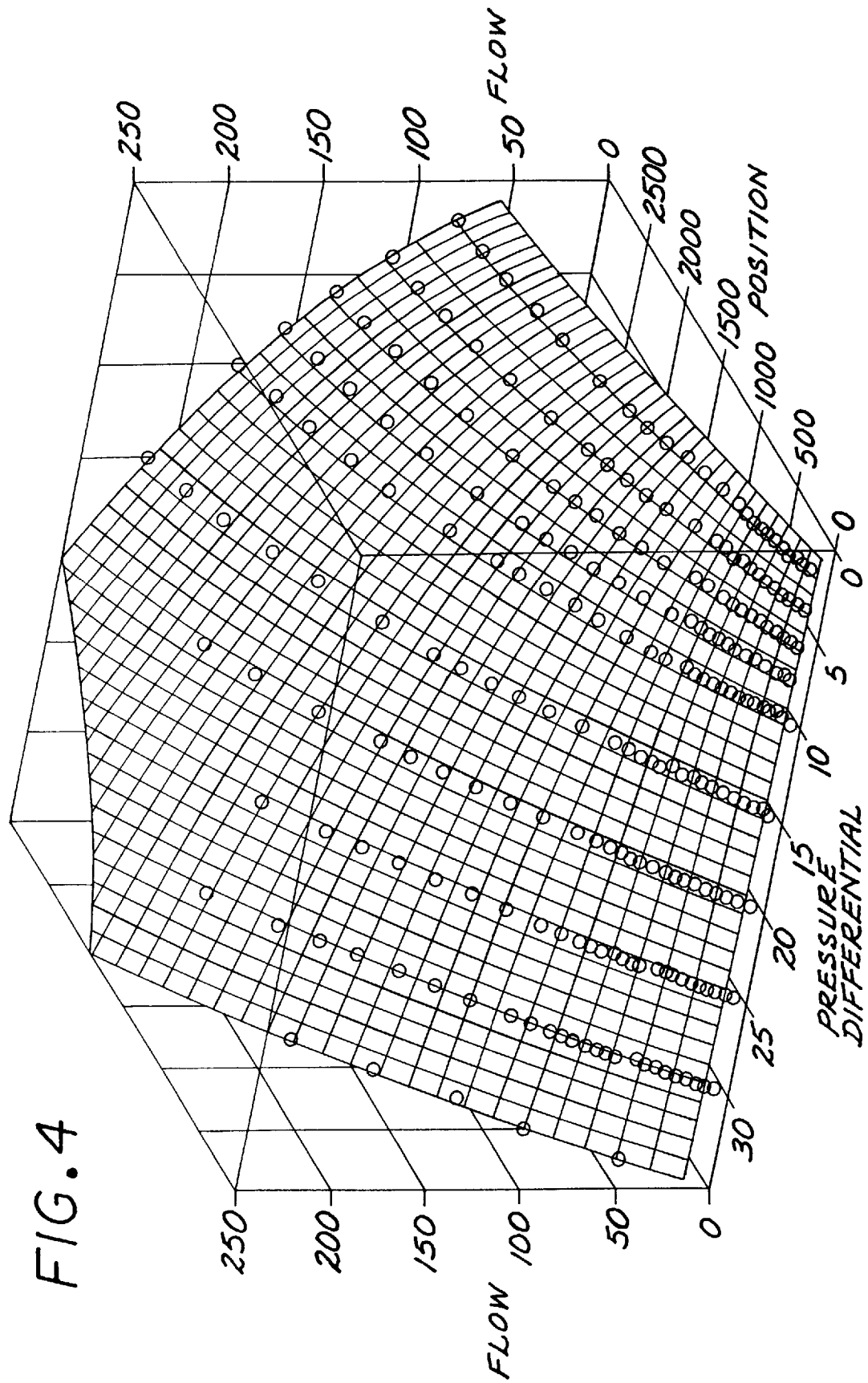
FIG. 4 is a three-dimensional diagram showing flow as a function of differential pressure and valve position.

Knowing f as a function of x and dp, the table of FIG. 4 can be rearranged to solve for step motor position as a function of flow and differential pressure:

$$x \propto \frac{f}{\sqrt{dp}} \tag{3}$$

This produces a position table (FIG. 5) which yields step motor position as a function of desired flow and differential pressure. As in the case of FIG. 4, intermediate values in the table of FIG. 5 can be ascertained by interpolation.

Figure 5:
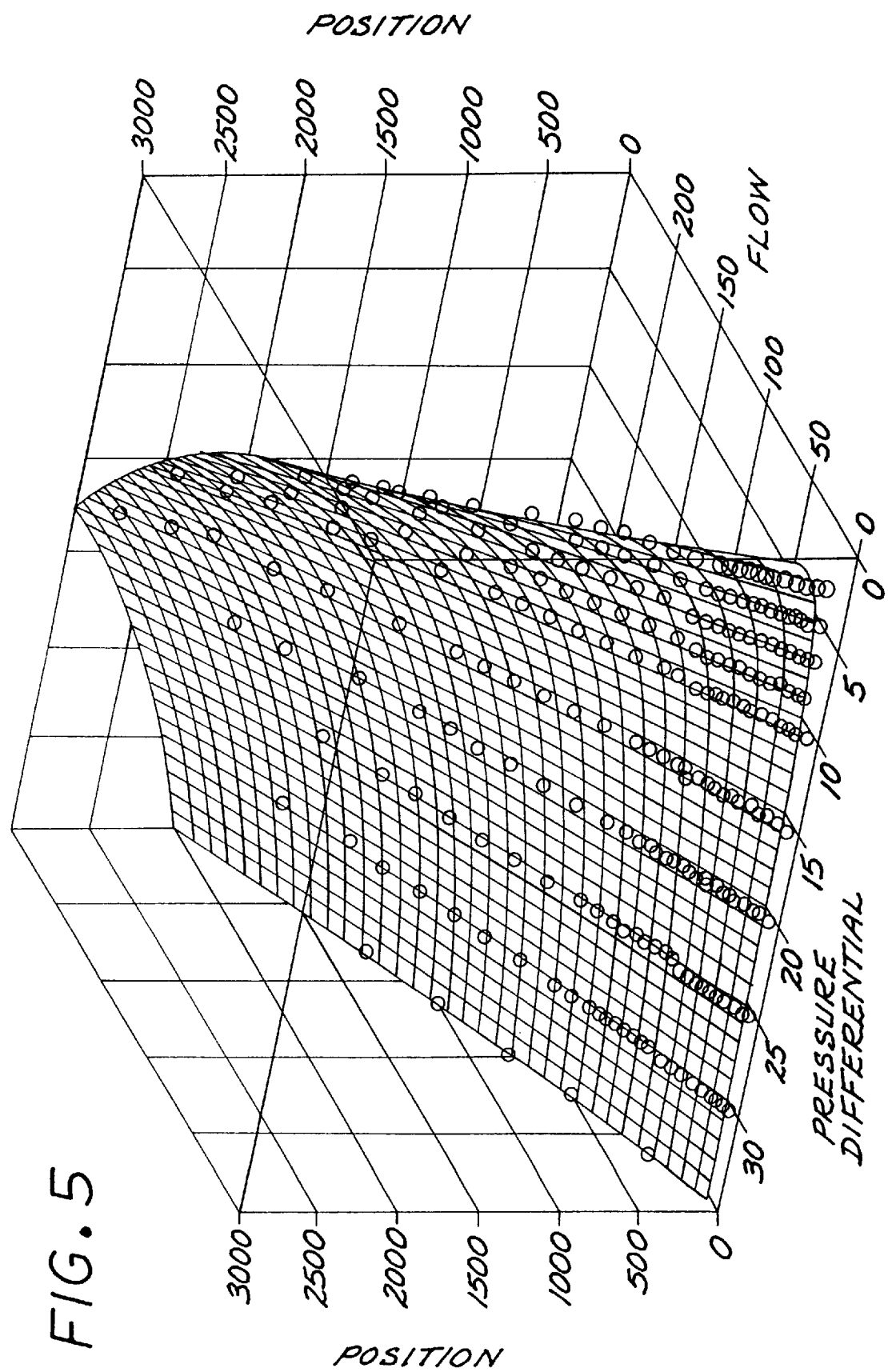
FIG. 5 is a three-dimensional diagram showing valve position for a desired flow in view of changes in differential pressure.

Because the flow f, and therefore the differential pressure dp, are themselves functions of the position x, the position calculation from the lookup table FIG. 5 must be continuously updated by the controller 82 to follow variations in the differential pressure, in order to deliver the desired flow. A typical iteration time in a preferred embodiment would be on the order of 2 ms.

It will be noted that the flow valve 12 functions both as a flow transducer (because flow, as a function of valve position and differential pressure, is known from the lookup table of FIG. 4) and a flow control (because it controls flow by its position). The sensed flow measurement produced by transducer 40 is independent of the flow valve. This flow signal is used to sense a patient effort for purposes of triggering a breath, and to measure the exhaled flow for the exhaled tidal volume display.

Figure 3:
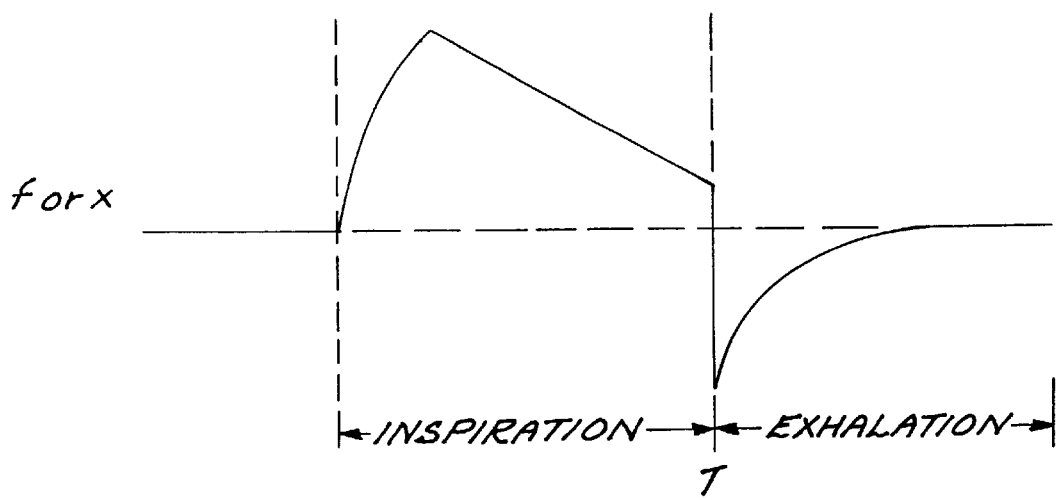
FIG. 3 is a time-flow diagram illustrating typical flow variations during a breathing cycle of a patient.

One of the factors that call for continuous iterative recalculation of the required position of step motor 80 is the fact that in most operational modes of the ventilator 10, inspiratory flow varies widely during the inspiration period. As seen in FIG. 3, which shows flow as a function of time for one breathing cycle in a typical operational mode, the flow (and consequently the valve position) rises sharply at the beginning of inspiration, then decreases as the patient's lungs fill. Inspiratory flow ends as determined by the selected mode and parameter settings, and is followed by exhalation, which is initiated by the release of exhalation drive solenoid 52.

It is understood that the exemplary ventilator system described herein and shown in the drawings represents only a presently preferred embodiment of the invention. Indeed various modifications and additions may be made to such embodiment without departing from the spirit and scope of the invention. Thus, other modifications and additions may be obvious to those skilled in the art and may be implemented to adapt the present invention for use in a variety of different applications.

What is claimed is:

1. A ventilator for patients needing assistance in breathing, comprising:

a) a compressor having an air input and an air output, and being arranged to compress said air at said output to a first pressure level;

b) a flow valve having an inlet and an outlet, and a valving element interposed therebetween, said air at said first pressure level being applied to said inlet, and said air exiting said outlet at a second pressure level;

c) a bypass valve arranged to receive a portion of said air at said first pressure level and to discharge said air into the input side of said compressor when said bypass valve is open;

d) said bypass valve being biased with a bias toward the closed position and being further so connected to said outlet of said flow valve that said bypass valve opens whenever said first pressure level exceeds the sum of said bias plus said second pressure level; and e) a conduit arranged to introduce said air exiting said outlet into the lungs of said patient.

2. The ventilator of claim 1, in which said compressor is a substantially constant speed compressor.

3. The ventilator of claim 1, in which said bias is a substantially constant bias.

4. The ventilator of claim 1, further comprising:

f) an actuator connected to said valving element for selectively increasing and reducing the air flow between said inlet and said outlet; and g) a controller operatively connected to said actuator to continuously cause said actuator to reposition said valving element in response to a selected air flow rate and the differential pressure between said first and second pressure level.

5. The ventilator of claim 4, in which said controller contains a lookup table of valving element positions corresponding to given air flow rates at given differential pressures, and said controller is arranged to continuously compute from said lookup table the valving element position necessary to produce a selected air flow at the current sensed differential pressure, and to control said actuator to so position said valving element.

6. The ventilator of claim 5, in which said lookup table contains empirically derived values.

7. The ventilator of claim 6, in which values intermediate to the empirically derived values are obtained by interpolation.

8. The ventilator of claim 5, in which said controller includes a second lookup table of air flow rates corresponding to given valving element positions at given differential pressures, and said controller is further arranged to continously compute from said second lookup table the air flow produced by the current valving element position at the current sensed differential pressure.

9. The ventilator of claim 8, in which said second lookup table contains empirically derived values.

10. The ventilator of claim 9, in which values intermediate to the empirically derived values in the second lookup table are obtained by interpolation.

11. The ventilator of claim 5, in which said actuator is a step motor.

12. The ventilator of claim 1, further comprising:

g) a source of oxygen under pressure;

h) a transducer arranged to measure the pressure of said oxygen source; and i) a digitally operated valve assembly connected to said oxygen source and arranged to mix a selected quantity of oxygen with said air in response to said measured source pressure.

13. A method for closed-loop control of air flow through a ventilator valve without measuring said air flow, comprising the steps of:

a) providing a valve with known flow path cross sections at various valve positions;

b) producing a pressure differential between the inlet and the outlet of said valve;

c) monitoring said pressure differential;

d) controlling the position of said valve in accordance with a control signal; and e) using said pressure differential and said control signal to adjust said control signal for producing a desired air flow.

14. The method of claim 13, in which said pressure differential is maintained substantially constant.

15. In a ventilator for patients needing assistance in breathing, a self-regulating flow control system, comprising:

a) a flow valve having an inlet and an outlet and defining a gas flow path between the inlet and the outlet, the flow valve including a valving element in the gas flow path that is movable through a plurality of positions, each of which defines a specific cross-sectional area of the gas flow path, whereby a differential pressure is developed between the inlet and the outlet, and a gas flow rate is generated through the outlet that is a function of the cross-sectional area of the gas flow path;

b) a pressure transducer in communication with the inlet and the outlet so as to generate a differential pressure signal indicative of the differential pressure; and c) a controller arranged to control the position of the valving element, the controller receiving the differential pressure signal and a position value indicative of the position of the valving element, wherein the controller, in response to the position value and the differential pressure signal, adjusts the position of the valving element for closed loop control of the gas flow rate.

16. The ventilator of claim 15, further comprising:

d) a bypass circuit including a biased valve and connecting the outlet of said flow valve to the inlet of said flow valve, said biased valve being so biased as to maintain a substantially constant pressure differential between the inlet and the outlet of said flow valve.

* * * * *